United States Patent
Rao et al.

(10) Patent No.: US 6,197,537 B1
(45) Date of Patent: Mar. 6, 2001

(54) METHOD FOR DETECTING PROTEASES AND USES THEREOF

(75) Inventors: Srinivasa K. Rao, New Hyde Park; Leslie Kushner, Forest Hill; Mahesh Mathrubutham, New Hyde Park; Jon R. Cohen, Lake Success, all of NY (US)

(73) Assignee: Long Island Jewish Medical Center, New Hyde Park, NY (US)

( * ) Notice: Subject to any disclaimer, the term of this patent is extended or adjusted under 35 U.S.C. 154(b) by 0 days.

(21) Appl. No.: 09/314,362

(22) Filed: May 19, 1999

Related U.S. Application Data (63) Continuation of application No. 09/049,667, filed on Mar. 27, 1998, now Pat. No. 6,017,723.

(51) Int. Cl.[7] .............................. C12Q 1/34; C12Q 1/37; C12Q 1/00
(52) U.S. Cl. .................... 435/23; 435/18; 435/4; 562/125
(58) Field of Search .................... 435/23, 18, 4; 562/125

(56) References Cited

U.S. PATENT DOCUMENTS 6,017,723 * 1/2000 Rao et al. .............................. 435/18

* cited by examiner

*Primary Examiner*—Louise N. Leary
(74) *Attorney, Agent, or Firm*—Amster, Rothstein & Ebenstein (57) ABSTRACT

The present invention provides an assay for detecting and quantifying protease that is sensitive, rapid, and capable of screening numerous samples of small volume. Also provided by the present invention is a method for diagnosing disorders associated with connective tissue destruction in a subject by detecting and quantifying a particular protease in a biological sample. Further provided by the present invention is a method of detecting inhibitors of the activity of a protease by detecting primary amines that are exposed by the enzymatic degradation of a protease substrate.

6 Claims, 4 Drawing Sheets

METHOD FOR DETECTING PROTEASES AND USES THEREOF

This application is a continuation of application Ser. No. 09/049,667, filed Mar. 27, 1998, now U.S. Pat. No. 6,017, 723 and entitled "Method for Isolating Inhibitors of Protease Activity". The contents of application Ser. No. 09/049,667 are incorporated herein by reference. This Application is a continuation of application Ser. No. 09/049,667, the contents of which are expressly incorporated herein by reference.

BACKGROUND OF THE INVENTION

Uncontrolled tissue destruction by protease release plays a role in some pathological conditions, and it is hypothesized that an imbalance in the protease antiprotease system is an important contributing factor. Elastase is a protease that is capable of hydrolyzing the connective tissue component elastin. Elastase acts on a protein's nonterminal bonds adjacent to an aliphatic amino acid. Elastase is one of the matrix degrading enzymes found in plasma and is closely associated with elastin tissue destruction found in conditions such as abdominal aortic aneurysm (AAA) (Cohn, J. R., et al. *Surg. Gynecol. Obstet.* 1987; 164:355–358); emphysema (Snider, G. L., et al. *Am. J. Resp. Crit. Case. Med.* 1994; 150:5131–5137); pancreatitis (Dominguez-Muneoz, J. E., et al. *Dig. Dis. Sci.* 1993; 38:507–513; Stein, J., et al. *Clin. Chem.* 1996; 42:222–226); and inflammatory conditions (Andus, T., et al. *Dig. Dis. Sci.* 1993; 38:1638–1644), such as arthritis.

Since abdominal aortic aneurysms often go unnoticed until they become large enough to be felt as a mass or to cause symptoms, a method for the early diagnosis of an abdominal aortic aneurism is needed, and would be extremely useful for early treatment of aneurysms.

In order to understand the role of elastase in these conditions one must be able to determine elastase activity. There are a variety of ways to quantitatively measure proteases, such as elastase, such as the use of radiolabeled elastin (Bieger, W., and Sheele, G. (1980) *Anal. Biochem.* 104, 239–246), second enzyme-coupled elastin (Saunders, G.C., Svitra, Z., and Martinez, A. (1982) *Anal. Biochem.* 126, 122–130), and synthetic substrates (Gertler, A., and Hofmann, T. (1970) *Can. J. Biochem.* 48, 384–386; Bieth, J., Spiers, B., and Wermuth, C. G. (1974) *Biochem. Med.* 11, 350–357; Zhou, D., Niewiarowski, S., and Stewart, G. J. (1995) *Anal. Biochem.* 224, 436–437), radioimmunoassay (Murata, A., Ogawa, M., Fugimoto, K-I, Kitahara, T., Matsuda, Y., and Kosaki, G. (1983) *Enzyme* 30, 29–37), zymography (Brophy, C. M., Sumpio, B., Reilly, J. M., and Tilson, D. M. (1991) *Surg. Res. Commun.* 10, 315–321), and ELISA (Dreher, M., Gunzer, R., Helger, R., and Lang, H. (1989) *Prog. Clin. Biol. Res.* 308, 707–710). However, these techniques have limitations, such as low sensitivity, they are time-consuming and labor-intensive, and they are unable to distinguish between elastase and zymogen (inactive enzyme) There is therefore an outstanding need for a rapid and sensitive method of detecting and measuring elastase in a sample for use in the understanding of the role of elastase in connective tissue disorders and for diagnosing connective tissue disorders.

Habeeb, A. F. S. A., *Anal.Biochem.* 14:328–336 (1966 describes a method of detecting the presence of free amino groups in proteins using 2,4, 6-trinitrobenzenesulfonic acid. Hatakeyama, et al. *Anal. Biochem.* 204:181–184 (1992) describe an assay for detecting protease using succinylcasein as a substrate. Bubnis and Ofner, *Anal. Biochem.* 207:129–133 (1992) describe the detection of ε-amino groups in proteinaceous material using trinitrobenzenesulfonic acid. These references do not, however, address the need for a method of determining specific inhibitors of elastase.

The role of elastase in connective tissue disorders may be better understood through the identification of inhibitors of elastase, since the loss of inhibition of elastase is an important contributing factor for the development of connective tissue disorders. Elastase may be inactivated by naturally occurring inhibitors that block the active site of the enzyme by binding tightly to it. These naturally occurring elastase inhibitors are necessary to prevent elastase from unnecessarily degrading proteins which can lead to connective tissue destruction. Once inhibitors of elastase are identified, they may be used in the design of drugs for treating these connective tissue disorders. Thus, an outstanding need remains for a method of detecting inhibitors of proteases, such as elastase, for the development of inhibitors for diagnosing and treating connective tissue disorders.

SUMMARY OF THE INVENTION

The present invention provides an assay for detecting and quantifying protease enzymes that is sensitive, rapid, and capable of screening numerous samples of small volume. The method provided by the present invention specifically detects and quantifies elastase in a biological sample by contacting the biological sample with a succinylated protease substrate, adding to the biological sample containing the substrate an amount of trinitrobenzenesulfonic acid (TNBSA) sufficient to detect the presence of primary amines in the sample, and measuring the amount of the primary amines. The amount of the primary amines in the sample is indicative of the amount of protease present therein.

Also provided by the present invention is a method for diagnosing disorders associated with connective tissue destruction in a subject by detecting and quantifying a particular protease in a biological sample.

The present invention provides a method of detecting inhibitors of the activity of a protease by detecting primary amines that are exposed by the enzymatic degradation of a protease substrate. Generally, the inhibitory effect of a substance on the activity of a protease is determined by introducing the substance into a reaction mixture containing a succinylated protease substrate, and the reaction is initiated by the addition of a known amount of a protease. The inhibitory effect of the substance is then evaluated by comparing the activity of the protease in the presence and absence of the substance.

The method of the present invention may be used to detect proteases such as elastase, other elastolytic enzymes, and trypsin by using substrates such as elastin, casein and gelatin. The method of detection may be used to detect proteases in biological samples including, but not limited to, whole blood, plasma, serum, synovial fluid, urine, saliva, sputum, mucous secretions, cell culture supernatant, tissue biopsies, and tissue homogenates.

Additional objects of the invention will be apparent from the description which follows.

BRIEF DESCRIPTION OF THE FIGURES

FIG. 1: FIG. 1 sets forth a time course of an elastase reaction. Succinylated elastin assay was carried out with 10 μg/ml (2.97 units/ml) (●), 1 μg/ml (0.297 units/ml) (■), and 100 ng/ml (0.0297 units/ml) (▲) of elastase. The digest was incubated at 37° C. for 0, 5, 10, 20, 30, and 60 minutes. Digests were prepared in duplicate and optical densities were read at 450 nm after the addition of TNBSA. Blank reaction contained buffer/enzyme. Blank reading was subtracted from the final reaction optical density to give corrected absorbance values.

FIGS. 2A and 2B: FIGS. 2A and 2B set forth the standard curve of elastase using succinylated elastin substrate. Succinylated elastin was treated with doubling dilutions of elastase from 2.97 to $2.97 \times 10^{-4}$ units/ml (10 μg/ml to 1 ng/ml). All dilutions were prepared from a 1 mg/ml stock of elastase and all dilutions were prepared in BupH buffer or 50 mM sodium borate, pH 8.0. Assays contained 50 μl of each enzyme dilution and 100 μg succinylated substrate and were brought up to a volume of 150 μl with BupH buffer or 50 mM sodium borate buffer, pH 8.0. Digests were incubated at 37° C. for one hour. All digests were prepared in quadruplicate and optical densities were measured at 450 nM. Blank reaction contained buffer/enzyme. Blank reading was subtracted from the final fraction optical density to give. corrected absorbance values. FIG. 2A shows a standard curve for elastase/succinylated elastin using 2.97 to 0.089 units/ml elastase, r=0.995.

FIG. 3: FIG. 3 shows assays which contained 100 μg succinylated elastin or casein; 50 μl of elastase or trypsin (0.1 mg/ml), 50 μl α1AT (10 mg/ml-0.001 mg/ml) and brought up to a final volume of 150 μl with 50 mM sodium borate pH 8.5. The samples were incubated at 37° C. for 30 minutes, and the OD was read at 450 nm. Elastase (●) r=0.92, Trypsin (■) r=0.97.

FIG. 4: FIG. 4 shows elastase in the presence of plasma (n=62, mean OD=0.152±0.012 SE) and absence of plasma (n=11, mean OD=1.12±0.028 SE) was assayed using 100 μg elastin, ±10 μl. plasma, 50 μl =elastase (1 mg/ml) in a final volume of 150 μl with 50 mM sodium borate pH 8.5 OD was read at 450 nm.

DETAILED DESCRIPTION OF THE INVENTION

The present invention provides an assay for detecting and quantifying protease in a sample. The assay presented herein is sensitive, rapid, and capable of screening numerous samples of small volume. Additionally, the assay of the present invention is simple, requiring three basic reagents, and uses easily available equipment. The rationale behind the assay is the use of a succinylated substrate for the protease to be detected, and the detection of primary amines which are exposed upon enzymatic digestion. Treatment with succinic anhydride blocks free primary amine groups on the side chains of amino acids on the protein (Hatakeyama, T., Kohzaki, H., and Yamasaki, N. (1992) *Anal. Biochem.* 204, 181–184). Primary amines are exposed due to the hydrolysis of peptide bonds in the substrate by the protease, which are detected by adding 2, 4, 6-trinitrobenzene sulfonic acid (TNBSA). TNBSA on interaction with primary amines produces a quantifiable color reaction (Bubnis, W. A., and Ofner, C. M. (1992) Anal. Biochem. 207, 129–133), the intensity of which is proportional to the number of unblocked amine groups available, which in turn is proportional to the activity of the protease. Therefore, the color reaction can be used to measure the protease activity in any given sample.

Specifically, the method provided herein detects the presence of a protease in a biological sample comprising the steps of contacting the biological sample with a succinylated protease substrate, then adding to the biological sample containing the substrate an amount of TNBSA sufficient to detect the presence of primary amines in the sample, and measuring the amount of the primary amines. The amount of the primary amines in the sample is indicative of the amount of protease present therein.

The method of the present invention may be used to detect proteases such as elastase and trypsin by using substrates such as elastin, casein and gelatin. The substrate may also be radiolabeled, or coupled to Sepharose.

The method of detection provided herein may be used to detect proteases in biological samples such as whole blood, plasma, serum, synovial fluid, urine, saliva, sputum, mucous secretions, cell culture supernatant, tissue biopsies, and tissue homogenates. The method provided herein can be used to detect protease in both purified samples and crude preparations.

The method of the present invention may be used to diagnose a disorder that is associated with connective tissue destruction in a subject. For example, by measuring the amount of elastase in a biological sample, such disorders as abdominal aortic anuerisms, urinary incontinence, and other disorders that result in the destruction of connective tissue can be diagnosed. The inventors have found that elastase activity in plasma taken from subjects suffering from abdominal aortic aneurysm is 8 times higher than the levels of elastase activity in plasma taken from normal individuals. The inventors also determined that elastase activity in plasma taken from individuals suffering from urinary incontinence is twice as high as levels of elastase in plasma taken from normal individuals.

This method is especially useful for the detection and quantification of elastase because it distinguishes between the active elastase enzyme and the inactive zymogen enzyme. The method of diagnosing a disorder in a subject as provided herein comprises obtaining a biological sample from the subject, contacting the biological sample with a substrate of the protease to be detected, then contacting the biological sample with TNBSA in an amount sufficient to bind to primary amines formed by the hydrolysis of peptide bonds in the substrate by the protease, and measuring the color resulting from the interaction of TNBSA with the primary amines.

Non-limiting examples of connective tissue disorders that can be diagnosed using the method described herein include such disorders as abdominal aortic aneurysms, atherosclerosis, emphysema, pancreatitis, glomerulonephritis, bronchial inflammation, systemic lupus erythematosus, rheumatism, and arthritis. The method of diagnosing a connective tissue disorder in a subject comprises detecting the presence of protease in a sample taken from a subject. Non-limiting examples of samples include whole blood, plasma, serum, synovial fluid, urine, saliva, sputum, or mucous secretions.

The present invention also provides a method of detecting inhibitors of the activity of a protease by detecting primary amines that are exposed by the enzymatic degradation of a protease substrate. Generally, the inhibitory effect of a substance on the activity of a protease is determined by introducing the substance into a reaction mixture containing a succinylated protease substrate, and the reaction is initiated by the addition of a known amount of a protease. The inhibitory effect of the substance is then evaluated by comparing the activity of the protease in the presence and absence of the substance.

Specifically, the method of detecting an inhibitor of a protease in a biological sample is determined by reacting the biological sample with a succinylated protease substrate to obtain a reaction mixture, reacting said reaction mixture with a known amount of protease to obtain a reaction mixture comprising primary amines, adding to said reaction mixture an amount of TNBSA sufficient to bind to said primary amines present in said mixture and to obtain a color reaction, and detecting the presence of an inhibitor in said reaction mixture by comparing the color intensity of said reaction mixture with a control reaction mixture.

Non-limiting examples of biological samples which may be used to detect inhibitors of protease include, but are not limited to, whole blood, plasma, serum, synovial fluid, urine, saliva, sputum, mucous secretions, cell culture supernatant, tissue biopsies, and tissue homogenates. The method provided herein can be used to detect inhibitors of protease in both purified samples and crude preparations.

In a specific embodiment of the invention, the method described herein is used to detect inhibitors of elastase. Since succinylated elastin has not been previously prepared, and conditions under which elastase digestion takes place was not previously known, these conditions were determined for the first time by the inventors. The inventors determined that phosphate buffered saline, boric acid, and sodium tetra borate provided the optimal buffer concentration and pH for elastase digestion of succinylated elastin.

The presence of an inhibitor of elastase in the reaction mixture may be determined by comparing the color intensity of said reaction mixture with a control reaction mixture.

The present invention is described in the following Experimental Details Section which is set forth to aid in the understanding of the invention, and should not be construed to limit in any way the invention as defined in the claims which follow thereafter.

Experimental Details Section

I. Materials and Methods

Biochemicals. Succinylated elastin and gelatin were prepared to final concentrations of 9 and 8 mg/ml, respectively, in 50 mM sodium borate buffer, pH 8.0. Succinylated casein, TNBSA (5% stock solution in water), BupH buffer, and trypsin were purchased as part of the Pierce Quanticleave™ protease assay kit II (Pierce Chemical Co., Rockford, Ill.). TNBSA was used as a 0.03% solution made up in BupH buffer or 50 mM sodium borate. Porcine pancreatic elastase (PPE; 297 units/mg) (EC 3.4.21.36) was purchased from CalBiochem (San Diego, Calif.). The elastin for succinylation was purchased from Elastin Products Co. (EPC, St. Louis, Mo.). The gelatin for succinylation was purchased from Sigma (St. Louis, Mo.).

Protein Succinylation. Proteins were succinylated using standard procedures as described by Hatakeyama et al. (Hatakeyama, T., Kohzaki, H., and Yamasaki, N. (1992) *Anal. Biochem.* 204, 181–184). Proteins were dissolved in 50 mM sodium borate buffer, pH 8.0, at a concentration of 10 mg/ml. Succinic anhydride was then added to the solution and the pH of the reaction was maintained at 8.0 by the addition of 1 M NaOH. After succinylation, excess reagent was removed by extensive dialysis against 50 mM sodium borate buffer, pH 8.0. Because dialysis will result in dilution of the proteins, the final concentration was determined by the BCA protein assay (Pierce Chemical Co.) using the modification described by Sorensen and Brodbeck (Sorensen, K., and Brodbeck, U. (1986) *Experimentia* 42, 161–162).

Assay Conditions. Elastase assay using succinylated elastin: A modified version of the method described in the Pierce Quanticleave™ protease assay kit II (Pierce Chemical Co.) was used for the elastase assay. The assay contained 100 μg of succinylated substrate (gelatin, elastin, or casein) and 50 of enzyme sample to be assayed, and the reaction was brought up to a final volume of 150 μl with BupH buffer or 50 mM sodium borate, pH 8.0 (50 mM sodium borate, pH 8.0, is a suitable substitute for BupH buffer). All reactions were prepared in 96-well Falcon 3097 flat-bottom microtiter plates (Beckton Dickinson, N.J.). The reactions were then incubated at 37° C. for 60 min. Fifty microliters of a 0.03% solution of TNBSA was then added to each reaction and left for 20 min at room temperature. The optical density of each reaction was then determined using a Bio-Whittaker microplate reader 2001 (Bio-Whittaker, Walkersville, Md.) at 450 nm. Blank reactions were also prepared which contained buffer and protease, buffer and substrate and buffer only. All sample dilutions were prepared in BupH buffer or 50 mM sodium borate buffer, pH 8.0, as were stock solutions of 1 mg/ml elastase and trypsin.

Elastase assay using Suc(Ala)3-nA (SANA). The following method was used for testing PPE (CalBio-chem) activity. A 25 mM stock solution of SANA (Sigma) in dimethyl sulfoxide (Sigma), 1 mg/ml stock solution of elastase in distilled water, and 0.2 M Tris buffer pH 8.0 with 0.1% Triton X-100(Sigma) was prepared. The assay contained 12 μl of SANA and 50 μl of the enzyme sample and was made up to 200 μl with 0.2 M Tris buffer. All reactions were prepared in 96-well Falcon 3097 flat-bottom microtiter plates (Beckton Dickinson) and carried out at room temperature. The optical density of each digest was recorded for 20 min, at 30 second intervals, at 405 nm using a Bio-Whittaker microplate reader 2001 (Bio-Whittaker).

Elastase assay using fluorescent (rhodamine)-labeled insoluble elastin. The following method was used for testing PPE (CalBiochem) activity. The assay contained 1 mg rhodamine-labeled elastin (Elastin Products Co.) and 330 μl of elastase solution (1000, 100, 10, 1, and 0.1 ng/ml) and was made up to 1 ml with 50 mM sodium borate buffer, pH 8.0. Digestion was carried out at 37° C. for 1 h. The reaction mixture was then centrifuged in a microcentrifuge for 20 min. Supernatant containing the digested elastin products (500 μl) was collected and the fluorescent signal was determined using excitation of 550 nm and emission of 570 nm, using a Shimadzu spectrofluorophotometer (Kyoto, Japan).

Time Course of Elastase/Elastin Reaction. A time course of the digestion of succinylated elastin by elastase was carried out by digesting 100 μg of succinylated elastin with 50 μl of 2.97, 0.297, and 0.0297 units/ml (10, 1, and 0.1 μg/ml) elastase at 37° C. for 0, 5, 10, 20, 30, and 60 min. Following incubation, 50 μl TNBSA was added to each reaction and left for 20 min at room temperature. The optical density of each reaction was then measured at 450 nm using a Bio-Whittaker microplate reader 2001 (Bio-Whittaker).

Measure of Elastase Activity in Normal Human Plasma. Plasma samples were prepared from the blood samples from normal volunteers collected in vacutainer tubes containing an anticoagulant. Elastolytic activity in the plasma samples was measured as follows. To 180 μl of plasma 120 μl of 3 M sodium chloride solution was added and incubated on ice for 30 min and centrifuged in a microcentrifuge (Fisher Scientific, Springfield, N.J.) for 10 min. The supernatant was then diluted (1:4) in 50 mM sodium borate buffer, pH 8.0, and used in the succinylated elastin assay.

II. RESULTS

Standard Curve. Proteolytic activity of elastase toward succinylated elastin is demonstrated in FIG. 1, where the hydrolysis of peptide bonds in succinylated elastin leads to the exposure of primary amino groups which in turn react with TNBSA to produce a color change that can be detected at 450 nm. Untreated elastin gave strong background ($A_{450=0.682}$ for 100 μg) because of the free amino groups available to react with TNBSA; however, succinylation of elastin will block most of these free amino groups. Consequently, succinylated elastin showed a fivefold reduction in the background absorbance compared to the absorbance produced by a similar amount of untreated elastin. Additionally, the increase in absorbance due to digestion was measurably greater than the absorbance due to background.

Figure 1:
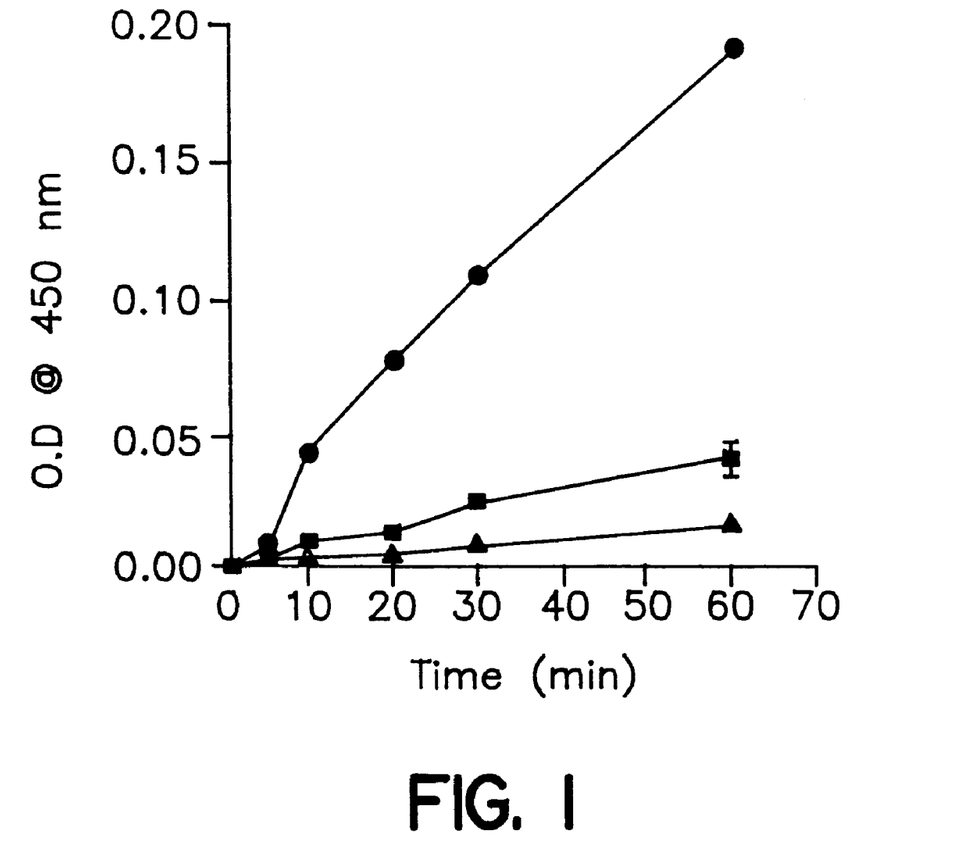

The rate of the enzyme reaction was initially determined by carrying out digest reactions for varying period of time for three different amounts of elastase. FIG. 1 shows that 2.97, 0.297, and 0.0297 units/ml (10, 1, and 0.1 μg/ml) elastase, the rate of reaction is linear up to 60 min. However, elastase activity could be detected after 30 min.

Figure 2A:
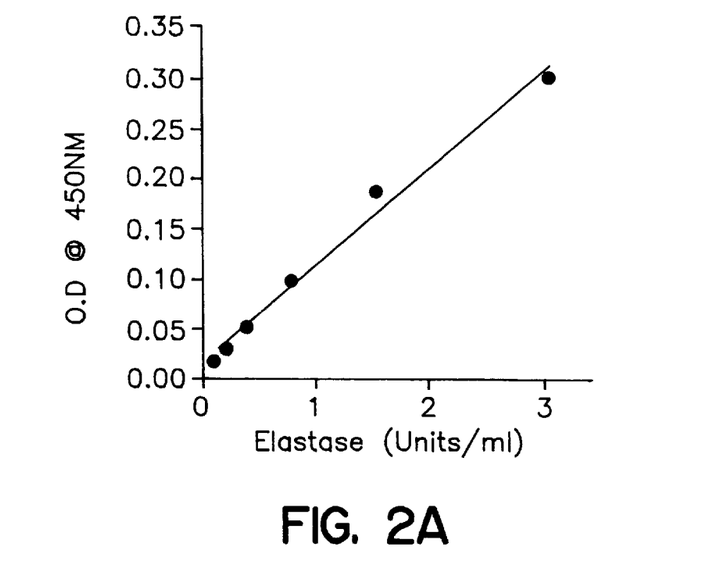
Figure 2B:
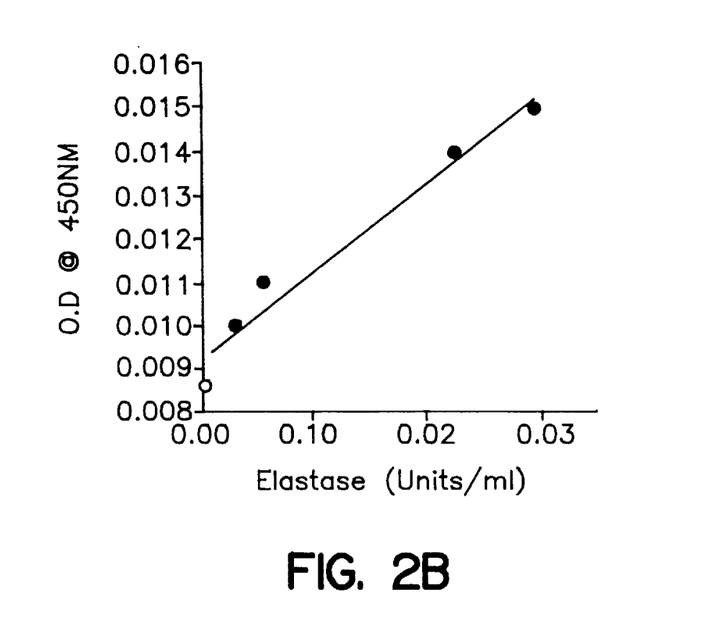
FIG. 2B shows a standard curve for elastase/succinylated elastin using 0.0297 to $2.97 \times 10^{-4}$ units/ml elastase, r=0.965.

FIGS. 2A and 2B show the increase in absorbance at 450 nm with increasing amounts of elastase. Doubling dilutions of elastase ranging from 2.97 units/ml (10 μg/ml) to 0.00297 units/ml (1 ng/ml) were used. Standard curve assays were carried out in quadruplicate and FIGS. 2A and 2B show that by using this assay the standard curve is linear from 1 ng/ml to 10 μg/ml.

Comparison of Elastase and Trypsin Substrate Affinities. Table 1 shows the rank order of substrate affinity of elastase and trypsin for each of the succinylated substrates, using two different amounts of protease. 10 μl and 1 μg/ml of elastase and trypsin were assayed using succinylated elastin, gelatin, and casein substrate. Enzyme dilutions were prepared from a 1 mg/ml stock of trypsin and elastase in BupH buffer or 50 mM sodium borate, pH 8.0. Assays contained 50 μl enzyme and 100 μg succinylated substrate and were made up to a volume of 150 μl with BupH buffer or 50 mM sodium borate buffer, pH 8.0. Digests were incubated at 37° C. for 1 hour. All digests were prepared in duplicate and optical densities were measured at 450 nm. Blank reaction contained buffer/enzyme. Blank reading was subtracted from the final reaction optical density to give corrected absorbance values. Standard deviations are given in parentheses. The activity of elastase varies with substrate in the following order: elastin>casein>gelatin. The activity of trypsin varies with substrate in the following order: gelatin>casein>elastin. Substrate affinity was evaluated by the level of absorbance at 450 nm each protease generated with each substrate.

| Comparison of Substrate Affinity for Elastase and Trypsin | | | | |
|---|---|---|---|---|
| | | Substrate | | |
| Protease | Concentration | Elastin | Casein | Gelatin |
| Elastase | 10 | 0.377 (±0.003) | 0.28 (±0.001) | 0.120 (±0.003) |
| | 1 | 0.085 (±0.003) | 0.071 (±0.006) | 0.037 (±0.001) |
| Trypsin | 10 | 0.049 (±0.011) | 0.158 (±0.002) | 0.354 (±0.006) |
| | 1 | 0.024 (±0.004) | 0.106 (±0.024) | 0.179 (±0.012) |

Comparison of Succinyl Elastin with SANA. The sensitivity of the succinylated elastin assay was compared to an elastase assay that uses SANA, a synthetic elastase substrate. 50 μl of 1000, 100, 10 and 1 ng/ml elastase was used to digest 100 μg of succinylated elastin and 12 μl of 12 mM SANA. The succinylated elastin digest was carried out at 37° C. for 1 hour. The SANA elastase assay was carried out at room temperature for 20 minutes. Optical densities were measured at 450 nm for succinylated elastin assay and 405 nm for SANA elastase assay. Blank reaction contained buffer/enzyme. Blank reading was subtracted from the final reaction optical density to give corrected absorbance values. Standard deviations are given in parentheses. Table 2 shows that although the use of SANA gave higher optical density readings at the highest concentrations of elastase, the use of succinylated elastin gave measurable levels of detection at elastase concentrations of 10 and 1 ng/ml, while SANA could not detect elastase activity less than 100 ng/ml in our assay protocol. In addition, data obtained with fluorescent-labeled insoluble elastin showed a detection sensitivity of 100 ng/ml, which reflects the sensitivity suggested by EPC (Elastin Products Company).

| Comparison of the Sensitivity of Elastase Assays Using Succinylated Elastin and the Synthetic Elastase Substrate | | |
|---|---|---|
| Elastase (ng/ml) | Succinylated Elastin | SANA |
| 1000 | 0.054 (±0.006) | 0.129 (±0.026) |
| 100 | 0.015 (±0.004) | 0.011 (±0.004) |
| 10 | 0.01 (±0.001) | 0 |
| 1 | 0.0086 (±0.003) | 0 |

Plasma Elastolytic Activity. Preliminary measurements of elastolytic activity were made using the succinylated elastin assay in 21 healthy volunteers, with ages ranging from 6 months to 71 years old. The elastolytic activity range was from no detectable activity to 14.77 μg/ml PPE equivalent enzyme activity.

III. DISCUSSION

Elastase activity in normal and pathological conditions such as emphysema and AAA is an important parameter. Therefore, there is a need for a better and more sensitive elastase assay, as well as an assay for identifying inhibitors of elastase. Succinylated elastin was employed with an aim to improve upon the present elastase assays. Table 1 shows that while succinylated elastin is efficiently digested by elastase, trypsin has very little effect on elastin, reflecting its specificity. The interaction between elastase and elastin has also been investigated by others (Vered, M., Burstein, Y., and Gertler, A. (1985) *Int. J. Peptide Protein Res.* 25, 76–84). Work showed that of the two types of elastase available, type I cleaves Ala-Ala and Ala-Gly, while type II cleaves Leu-Ala, Leu-Gly, Phe-Ala, Tyr-Ala, and Tyr-Gly (Vered, M., Burstein, Y., and Gertler, A. (1985) *Int. J. Peptide Protein Res.* 25, 76–84). However, even though trypsin is closely related to elastase, it digests elastin inefficiently. Unlike elastin, both gelatin and casein are digested by a wide variety of proteases and as expected both elastase and trypsin digested succinylated gelatin and casein, albeit to varying degrees.

All the steps presented herein can be carried out in microtiter plate wells, which offers a number of advantages. First, the assay requires only small amounts of sample and substrate, therefore maximizing the use of sample and reagents. Second, numerous samples can be assayed simultaneously. Third, the optical density of each reaction can be instantaneously analyzed after the final incubation with TNBSA. This is particularly important when many samples are assayed because any delay in obtaining absorbance values may lead to erroneous results. Additionally, 50 mM sodium borate buffer, pH 8.0, was found to be a suitable substitute for BupH buffer because both produced comparable standard curves for elastase in this assay, while phosphate-buffered saline, pH 7.5, was an unsuitable buffer for this assay (data not shown).

This assay is. also versatile because it can be used to detect elastase activity in purified samples or in crude samples, such as blood plasma. The variation observed in the preliminary analysis of plasma elastolytic activity indicates that it rises with age as in previous reports (Robert, L. (1988) *Pathol. Biol.* 36, 1101–1107). The assay was also used to measure elastolytic activity in cell culture supernatant, tissue biopsies, and tissue homogenates (Badlani and Singhal, personal communication). Additionally, the basic rationale behind this assay may also be applied to the detection of any protease with its succinylated substrate. This aspect of the assay was also investigated through the use of succinylated gelatin and casein, which were found to be digested efficiently by trypsin and to a lesser extent by elastase because elastase showed the greatest activity against elastin.

In comparison to other elastase assay methods, the succinylated elastin assay is superior to the use of synthetic elastase substrates because the succinylelastin assay is at least 50 times more sensitive than the use of SANA as shown in this paper and by other work (Bieth, J., Spiers, B., and Wermuth, C. G. (1974) *Biochem. Med.* 11, 350–357). Also elastin is a more biologically significant substrate for elastase than SANA. The interaction between elastin and elastase would also be more biochemically relevant than interactions between elastase and SANA.

With relation to other techniques that use elastin, such as radiolabeled soluble elastin (Bieger, W., and Sheele, G. (1980) *Anal. Biochem.* 104, 239–246), or soluble radiolabeled elastin coupled to Sepharose (Rifkin, D. B., and Crowe, R. M. (1977) *Anal. Biochem.* 79, 268–275), the microplate assay not only offers increased sensitivity, but also simplifies quantitation of elastase activity and is less labor-intensive and time-consuming. Radioimmunoassays, zymography, and ELISA assays for elastase (Murata, A., Ogawa, M., Fugimoto, K-I, Kitahara, T., Matsuda, Y., and Kosaki, G. (1983) *Enzyme* 30, 29–37; Brophy, C. M., Sumpio, B., Reilly, J. M., and Tilson, D. M. (1991) *Surg. Res. Commun.* 10, 315–321; Dreher, M., Gunzer, R., Helger, R., and Lang, H. (1989) *Prog. Clin. Biol. Res.* 308, 707–710) are also available. The disadvantage of radioimmunoassays and ELISA assays is that they are unable to distinguish between active elastase and inactive zymogen. However, the succinylated elastin assay detects elastin digestion products by measuring the release of primary amines. Therefore, it will only detect active elastase. Alternatively, zymography (Brophy, C. M., Sumpio, B., Reilly, J. M., and Tilson, D. M. (1991) *Surg. Res. Commun.* 10, 315–321) is sensitive and will detect in gel elastin digestion following gel electrophoresis. However, this process of elastase detection is not conducive to high capacity screening because it is limited by the number of wells that are available per gel, and it is time-consuming because it requires gel electrophoresis and protracted gel washing and in-gel digestion periods.

A limitation of the succinylated elastin assay is related to the reactivity of TNBSA. Because TNBSA reacts with primary amines, protease solutions or buffers used in the assay must be free of intrinsic amine content. For example, 10 mM Tris is known to react with TNBSA to generate unfavorable levels of background (Hatakeyama, T., Kohzaki, H., and Yamasaki, N. (1992) *Anal. Biochem.* 204, 181–184). Under such circumstances, samples can be diluted prior to use such that the background is reduced to a-suitable level. The level of protease activity can then be determined by subtracting the background value from the final optical density of the reaction. It must be also considered that succinylation may alter the natural affinity to the enzyme. However, the fact that activity could be detected with 50 pg of elastase in a 150-$\mu$l assay, and the specificity of elastase is well maintained in comparison with the other substrates, casein and gelatin, indicates that the elastin substrate is suitable for detection of elastase activity.

The succinylated elastin assay presented herein offers a reliable and sensitive assay for elastase that will be useful for further studies. Variations in plasma elastase and plasma proteolytic activity are associated with aging and disease conditions. As individuals age, studies have indicated that elastase activity increases with age (Robert, L. (1988) *Pathol. Biol.* 36, 1101–1107). The versatility of the succinylated elastin assay offers a method of investigating this variation and also variations with respect to disease conditions. An important pathological condition associated with elastase activity, and possibly the age-dependent increase in elastase activity, is AAA (Cohen, J. R., Mandell, C., Margolis, I., Chang, J., and Wise, L. (1987) *Surg. Gynecol. Obstet.* 164, 355–358; Grand Rounds (1993) *Lancet* 341, 215–220; Rao, S. K., Reddy, V., and Cohen, R. J. (1996) *Ann. NY Acad. Sci.* 800, 131–137). This assay will also be useful in studying the influence of elastin-derived peptides (EDP) on elastase/elastin interaction because EDPs are known to be involved in the regulation of elastase activity (Tyagi, S.C., and Sanford, S. R. (1993) *J. Biol. Chem.* 268, 16513–16518; Sarfati, I., Lopez, D., Murphy, A. E., Rao, S. K., and Cohen, J. (1996) *J. Surg. Res.* 61, 84–88). Finally, any sensitive technique for elastase detection will provide new insights into the understanding of the pathobiology of elastase.

Inhibition Assay. The inhibition assay contained 100 $\mu$g succinylated elastin, 10 $\mu$l plasma, 50 $\mu$l porcine pancreatic elastase (PPE; E.C. 3.4.21.36; 1 mg/ml made up in 50 mM sodium borate buffer pH 8.5; 297 units/mg; Calbiochem, San Diego, Calif.) and was brought up to a final volume of 150 $\mu$l with 50 mM sodium borate buffer pH 8.5, in a 96 well microplate (one unit of enzyme will hydrolyze 1 $\mu$mol of N-Ac-(Ala)-methyl ester per minute at 25° C., pH 8.5). The assay was carried out at 37° C. for 30 minutes. Subsequently 50 $\mu$l of 0.03% trinitrobenzene sulfonic acid (TNBSA; Pierce Chemical Co., Rockford, Ill.) was added and left for 20 minutes at room temperature. Optical densities (O.D.) were measured at 450 nm as previously described (Rao, S. K., et al. *Anal. Biochem.* 250:222–227 (1997)).

For each plasma sample analyzed, a corresponding blank was prepared containing 10 $\mu$l plasma, 10 $\mu$l PPE, buffer up to 150 $\mu$l, without succinylated elastin. The blank was treated in the same way as the experimental reaction. It is critical to include blanks, as they indicate the intrinsic amine content present in the sample. The blank O.D. can then be subtracted from the experimental reaction to evaluate the inhibitory capacity of the plasma sample. A comparison of the blank O.D. (n=62, mean=1.46±0.020 SE) with that of the experimental reactions (n=62, mean±1.61±0.025 SE) by one way ANOVA, using the INSTAT statistics program, shows that the difference between the two groups is statistically significant (p<0.001). This indicates that the difference between the blank and experimental O.D. is attributable to plasma inhibition of elastase and not due to background noise.

Positive controls were also used to show that the assay could detect elastase inhibition. The inhibitory effect of α-1-antitrypsin (α1AT;1000 units/mg; Sigma, St. Louis, Mo.) on 500 ng PPE and trypsin (13564 units/mg; Pierce Chemical Co.) was also evaluated. When trypsin was used in the inhibition assay, 50 µl succinylated casein (2 mg/ml in 50 mM sodium borate buffer pH 8.5; Pierce Chemical Co.) was used as the substrate.

Plasma samples were prepared from blood samples collected in vacutainer tubes (containing sodium heparin) from normal healthy volunteers, in accordance with the institutional review board committee guidelines and approval. Volunteers were aged between 16 and 84 years (n=62). Normal volunteers were individuals who had no clinical symptoms or signs of any connective tissue disorders. Plasma was prepared and assayed following blood collection. Plasma can also be stored at −70° C. without significant loss of inhibitory capacity. However, repeated freeze thawing does reduce plasma inhibitory capacity by approximately 2% per freeze-thawing event. Storage of plasma at 4° C., −20° C. or at room temperature overnight appears to adversely affect plasma inhibition in comparison to storage at −70° C. All reagents for the assay were kept on ice at all times during the assay.

Figure 3:
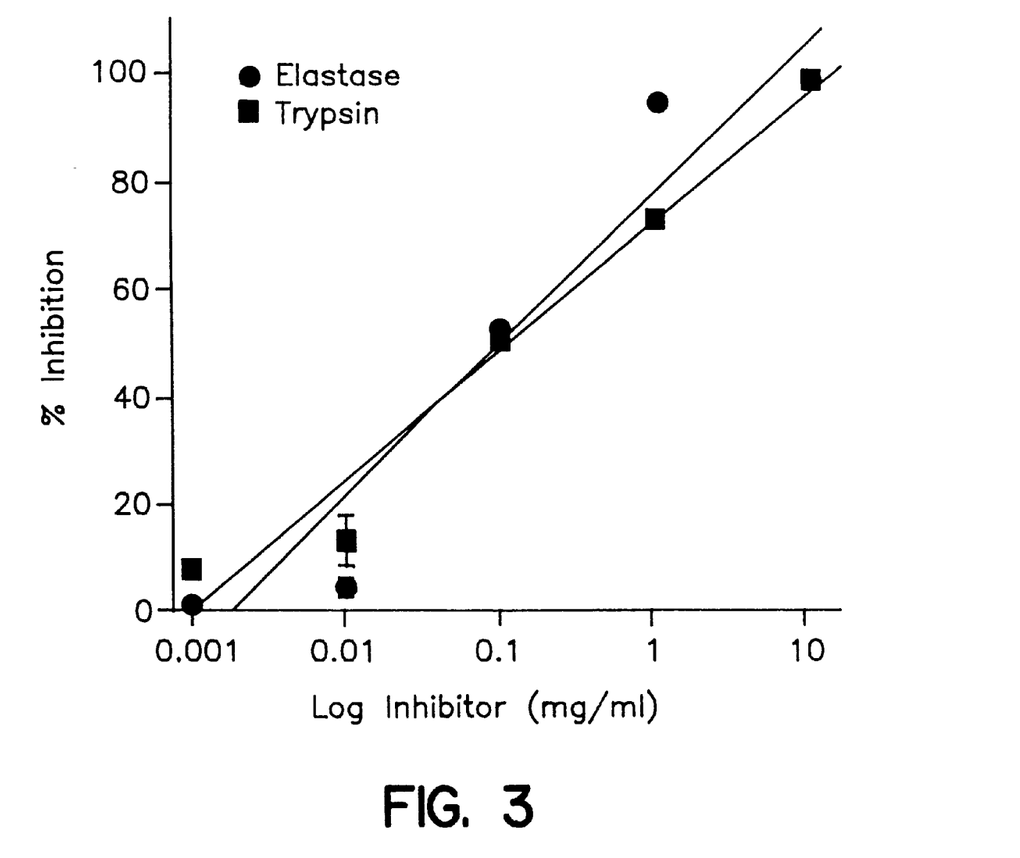
FIG. 3 sets forth the results of an inhibition assay using α1AT.

Initially the percentage inhibition of elastase and trypsin by the protease inhibitor, α1AT, was investigated. Using different (w/w) ratios of protease to inhibitor, the relative activity of a constant amount of elastase and trypsin in the presence and absence of a varying amount of α1AT was determined. From this comparison, the percentage inhibition by the inhibitor was calculated. The results are shown in FIG. 3, and indicate that this assay may be used to detect elastase inhibition and may also be applied to the evaluation of inhibition of other proteases.

The inhibitory capacity of plasma from normal individuals was then studied. The data (FIG. 4) suggest that the components of plasma from normal volunteers significantly inhibit the added elastase. The mean percentage inhibition in the normal group was 86.36% (n=62, ±1.11 SE) and reflects the low variation in plasma inhibitory capacity expected in normal individuals who are considered to have a normal protease antiprotease balance. The interassay variation with respect to plasma inhibition was ±2.81 SE (mean % inhibition=71.21%) at the 95% confidence interval. In relation to α1AT against PPE (FIG. 1A) 86.36% inhibition is equivalent to 42.8 µg α1AT in 10 µl plasma.

The relevancy of changes in elastase activity in pathological conditions has been inconclusive possibly because the methodology of measuring elastase activity is insensitive to small changes. Therefore, the inventors developed a novel and sensitive method to determine the ability of plasma to inhibit purified elastase activity. By introducing plasma and purified elastase into the assay, the elastase inhibition potential of plasma and other substances can be determined.

The assay was initially assessed by looking at the inhibition of elastase and trypsin by the protease inhibitor α1AT. As shown in FIG. 3, the optimum inhibitory w/w ratio of α1AT:elastase was 100:1 (50:1 molar ratio equivalent). However, previous studies suggested that elastase is inhibited by alAT at a molar ratio of 1:1 (Gustavsson, E. L., et al. *Physiol. Chem.* 1980 361:169–176). This difference may be due to the highly purified PPE that was used, which may require a greater amount of inhibitor to inhibit a given amount of elastase. PPE is from porcine source while α1AT is from human source, therefore, the elevated inhibitor:protease ratio may be a manifestation of this difference. The elastase inhibition assay conditions also favors elastase activity over α1AT, as pH, buffer and excess substrate are used, and so may cause the inhibitory ratio to increase. The data obtained for trypsin inhibition shows that the optimum ratio is 10:1 inhibitor:protease. This is close to the commercial specifications, which suggest that a ratio of 7.5:1 is inhibitory.

Figure 4:
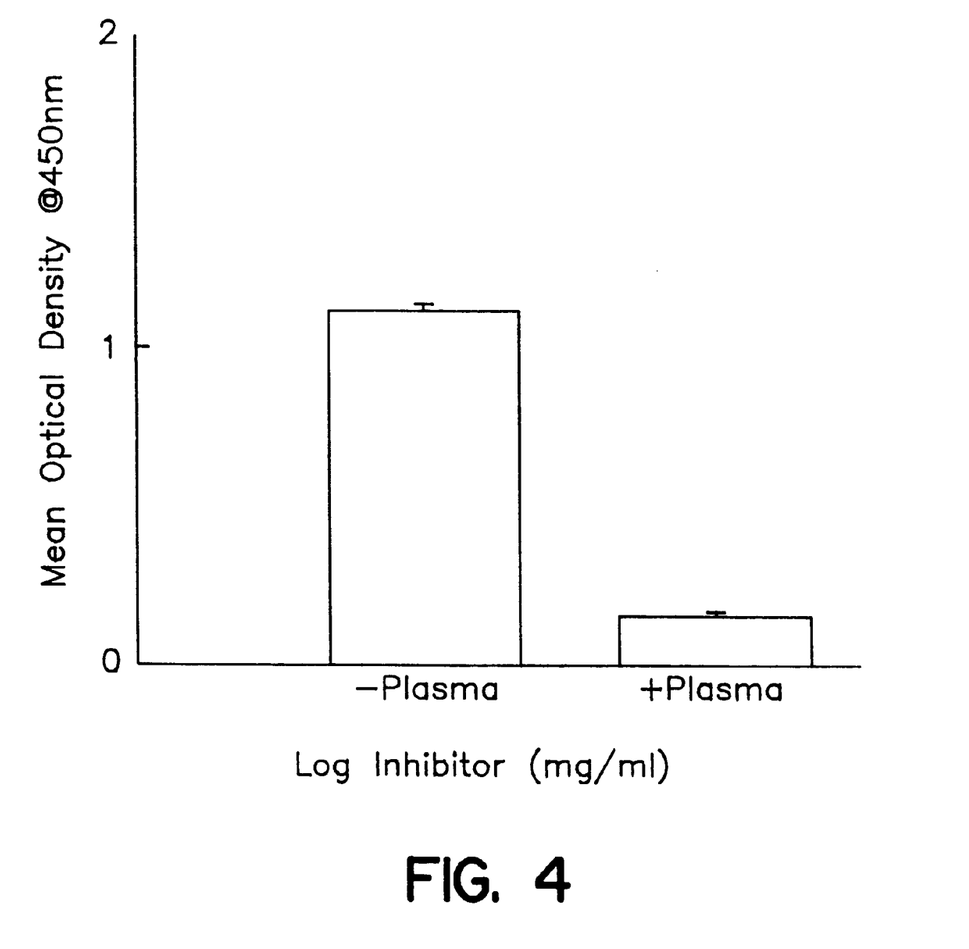
FIG. 4 sets forth the results of an inhibition assay using plasma from normal volunteers.

Having established that inhibition could be detected, plasma was analyzed from normal volunteers for elastase inhibition. It has been hypothesized that one of the factors that promote connective tissue destruction in connective tissue disorders is an imbalance in the protease antiprotease system (Schmid, S., et al. Scand. *J. Gastroenterol.* 1996; 31 suppl 219:47–50). Therefore, normal individuals who are not subject to such conditions should be capable of efficiently suppressing elastase. The data obtained using normal plasma confirms this. The inhibition assay presented herein is capable of quantifying elastase inhibition and indicates that components of normal plasma appear to be able to suppress elastase activity (FIG. 4). The assay may be used to analyze plasma from patients with connective tissue disorders where a loss of inhibitory control is a characteristic feature. These patients should have a lowered plasma inhibitory capacity, therefore the relative activity of exogenous elastase will be greater in the presence of patient plasma compared to age matched normal plasma. Exogenous elastase is added to plasma to attempt to emulate the localized release of excess elastase, by circulating cells and resident cells, under certain disease conditions.

All publications mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for detecting the presence of a protease in a biological sample comprising the steps of:

(a) contacting the biological sample with a succinylated protease substrate to obtain a reaction mixture;

(b) adding to the reaction mixture an amount of trinitrobenzenesulfonic acid (TNBSA) in an amount sufficient to detect the presence of primary amines in the reaction mixture; and (c) measuring the amount of primary amines in the reaction mixture, wherein the amount of primary amines measured is indicative of the amount of protease.

2. The method of claim 1, wherein the substrate is selected from the group consisting of elastin, casein and gelatin.

3. The method of claim 1, wherein the biological sample is selected from the group consisting of whole blood, plasma, serum, synovial fluid, urine, saliva, sputum, mucous secretions, cell culture supernatant, tissue biopsies, and tissue homogenates.

4. A method of diagnosing a connective tissue disorder in a subject, comprising the steps of:

(a) contacting a biological sample obtained from the subject with a succinylated protease substrate to form a reaction mixture;

(b) contacting the biological sample with trinitrobenzenesulfonic acid (TNBSA) in an amount sufficient to detect the presence of primary amines in the reaction mixture;

(c) measuring the amount of primary amines in the reaction mixture, wherein the amount of primary amines measured is indicative of the amount of protease; and (d) comparing the amount of protease detected in the biological sample to a standard amount of protease detected in a normal subject, wherein an elevated level of protease in relation to the standard amount is indicative of a connective tissue disorder.

5. The method of claim 4, wherein the biological sample is selected from the group consisting of whole blood, plasma, serum, synovial fluid, urine, saliva, sputum, and mucous secretions.

6. The method of claim 4, wherein the elevated level of protease detected in the subject indicates an abdominal aortic aneurysm, artherosclerosis, emphysema, pancreatitis, glomerulonephritis, bronchial inflammation, systemic lupus erythematosus, rheumatism, or arthritis.

* * * * *